United States Patent [19]

Gluchowski

[11] Patent Number: 5,077,292
[45] Date of Patent: Dec. 31, 1991

[54] (2-IMIDAZOLIN-2-YLAMINO) TETRAHYDROQUINOXALINES AND METHODS FOR USING SAME

[75] Inventor: Charles Gluchowski, Mission Viego, Calif.

[73] Assignee: Allergan, Inc., Irvine, Calif.

[21] Appl. No.: 420,817

[22] Filed: Oct. 12, 1989

[51] Int. Cl.$^5$ ............... C07D 403/12; A61K 31/495
[52] U.S. Cl. .................................. 514/249; 544/353; 564/305
[58] Field of Search ..................... 544/353; 514/249

[56] References Cited

U.S. PATENT DOCUMENTS 3,890,319 7/1975 Danielewicz et al. ............ 544/353

FOREIGN PATENT DOCUMENTS 2538620 3/1976 Fed. Rep. of Germany .

OTHER PUBLICATIONS

Gellai et al., Renal Effects of Selective Alpha-1 and Alpha-2 Adrenoceptor Agonists in Conscious, Normotensive Rats, J. of Pharmcol. & Experimental Therapeutics, 240, p. 723 (1987).
Fondacaro et al., Selective Alpha-2 Adrenoceptor Agonists Alter Fluid and Electrolyte Transport in Mammalian Small Intestine, J. of Pharmcol. & Experimental Therapeutics, 247, p. 481 (1988).
Burke et al., Ocular effects of a relatively selective Alpha-2 agonist (UK-14, 304-18) in cats, rabbits and monkeys, Current Eye Research, 5, p. 665 (1986).
Jumblatt et al., Alpha-2 adrenergic modulation of norepinephrine secretion in the perfused rabbit iris-ciliary body, Current Eye Research, 6, p. 767 (1987).
Mittag, PhD., Ocular Effects of Selective Alpha-Adrenergic Agents: A New Drug Paradox?, Annals of Ophthalmology, p. 201, (Mar., 1983).
Gellai et al., Mechanism of Alpha-2-adrenoceptor agonist-induced diuresis, Am. J. Physiol., p. F317 (1988).
Timmermans et al., Clonidine and some bridge analogues; cardiovascular effects and nuclear magnetic resonance data (H/C), Eur. J. Med. Chem., 15, p. 323 (1980).
Isom et al., Alpha-2-Adrenergic Receptors Accelerate Na/H Exchange in Neuroblastoma X Glioma Cells, J. Biol. Chem., 262, p. 6750 (1987).
Fielding et al., Clonidine: New Research in Psychotropic Drug Pharmacology, from Medicinal Research Reviews, vol. 1, pp. 97-123 (1981).
Jarrott, Clonidine and related compounds, from Handbook of Hypertension, vol. 5, p. 113 (1984).
Dharmsathaphorn, Alpha-2 Adrenergic Agonists: A Newer Class of Antidiarrheal Drug Gastroenterology 1986:91:769-775.

Primary Examiner—John M. Ford
Assistant Examiner—E. Bernhardt
Attorney, Agent, or Firm—Gordon L. Peterson; Frank J. Uxa, Jr.

[57] ABSTRACT

A compound selected from the group consisting of those having the formula:

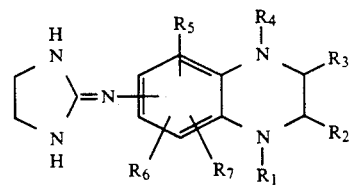

and pharmaceutically acceptable acid addition salts thereof, wherein $R_1$ wherein $R_1$ and $R_4$ are independently selected from the group consisting of H and alkyl radicals containing 1 to 4 carbon atoms, $R_2$ and $R_3$ are independently selected from the group consisting of H, OXO, and alkyl radicals containing 1 to 4 carbon atoms, the 2-imidazolin-2-ylamino group may be in any of the 5-, 6-, 7- or 8- positions of the quinoxaline nucleus, and $R_5$, $R_6$ and $R_7$ each is located in one of the remaining 5-, 6-, 7- or 8- positions of the qunioxaline nucleus and is selected from the group consisting of Cl, Br, H and alkyl radicals containing 1 to 3 carbon atoms. Such compounds, when administered to a mammal, provide desired therapeutic effects, such as alteration in the rate of fluid transport in the gastrointestinal tract, reduction in intraocular pressure, and increase in renal fluid flow.

32 Claims, No Drawings

(2-IMIDAZOLIN-2-YLAMINO) TETRAHYDROQUINOXALINES AND METHODS FOR USING SAME

BACKGROUND OF THE INVENTION

The present invention relates to novel substituted derivatives of quinoxaline. More particularly, the invention relates to such derivatives which are useful as therapeutic agents, for example, to effect reduction in intraocular pressure, to increase renal fluid flow and to effect an alteration in the rate of fluid transport in the gastrointestinal tract.

Various quinoxaline derivatives have been suggested as therapeutic agents. For example, Danielewicz, et al U.S. Pat. No. 3,890,319 discloses compounds as regulators of the cardiovascular system which have the following formula:

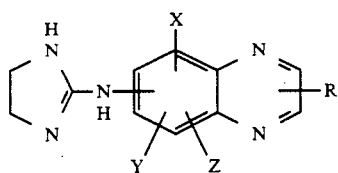

where the 2-imidazolin-2-ylamino group may be in any of the 5-, 6-, 7- or 8- position of the quinoxaline nucleus; X, Y and Z may be in any of the remaining 5-, 6-, 7- or 8- positions and may be selected from hydrogen, halogen, lower alkyl, lower alkoxy or trifluoromethyl; and R is an optional substituent in either the 2- or 3- position of the quinoxaline nucleus and may be hydrogen, lower alkyl or lower alkoxy.

SUMMARY OF THE INVENTION

The novel compounds of the present invention are those having the formula:

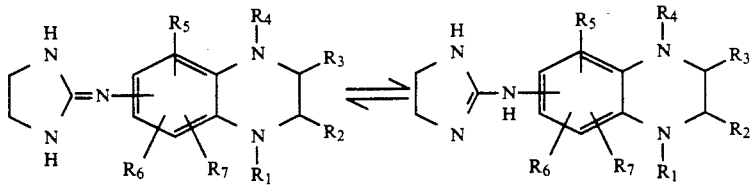

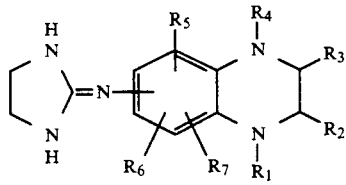

and pharmaceutically acceptable acid addition salts thereof, wherein $R_1$ and $R_4$ are independently selected from the group consisting of H and alkyl radicals containing 1 to 4 carbon atoms, $R_2$ and $R_3$ are independently selected from the group consisting of H, O, and alkyl radicals containing 1 to 4 carbon atoms, the 2-imidazolin-2-ylamino group may be in any of the 5-, 6-, 7- or 8- positions, preferably in the 6- position, of the quinoxaline nucleus, and $R_5$, $R_6$ and $R_7$ each is located in one of the remaining 5-, 6-, 7- or 8- positions of the quinoxaline nucleus and is independently selected from the group consisting of Cl, Br, H and alkyl radicals containing 1 to 3 carbon atoms.

Particularly useful compounds are those in which $R_1$ and $R_4$ are H, $R_2$ and $R_3$ are independently selected from the group consisting of H and alkyl radicals containing 1 to 4 carbon atoms, the 2-imidazolin-2-ylamino group is in the 6-position of the quinoxaline nucleus, $R_5$ is selected from the group consisting of Cl, Br and alkyl radicals containing 1 to 3 carbon atoms, more preferably Br, and is in the 5- position of the quinoxaline nucleus, and $R_6$ and $R_7$ are H.

Pharmaceutically acceptable acid addition salts of the compounds of the invention are those formed from acids which form non-toxic addition salts containing pharmaceutically acceptable anions, such as the hydrochloride, hydrobromide, hydroiodide, sulphate or bisulfate, phosphate or acid phosphate, acetate, maleate, fumarate, oxalate, lactate, tartrate, citrate, gluconate, saccharate and p-toluene sulphonate salts.

The present compounds provide one or more therapeutic effects, e.g., in mammals. Thus, these compounds are useful in a method for treating a mammal in which one or more of these compounds are administered to a mammal in an amount sufficient to provide the desired therapeutic effect in the mammal. Among the desired therapeutic effects provided by the present compounds include altering the rate of fluid transport in the gastrointestinal tract of a mammal; reducing or maintaining the intraocular pressure in at least one eye of a mammal; and increasing the renal fluid flow in at least one kidney of a mammal.

DETAILED DESCRIPTION OF THE INVENTION

The compounds of the present invention, i.e., 2-imidazolin-2-ylamino tetrahydroquinoxalines, are as described above. All stereoisomers, tautomers and mixtures thereof which comply with the constraints of one or more formulae of the present compounds are included within the scope of the present invention. For example, both tautomers are within the scope of the present invention.

The present compounds may be prepared in a manner analogous to the procedures described in Danielewicz, et al U.S. Pat. No. 3,890,319 for the production of the quinoxaline derivatives therein. This patent is hereby incorporated in its entirety by reference herein. Once a 2-imidazolin-2-ylamino quinoxaline intermediate corresponding to the compound described in Danielewicz, et al U.S. Pat. No. 3,890,319 is obtained, this 2-imidazolin-2-ylamino quinoxaline intermediate is hydrogenated to saturate any unsaturation at the 1-, 2-, 3-, and 4- positions of the quinoxaline nucleus.

Briefly, the 2-imidazolin-2-ylamino quinoxaline intermediates may be prepared by (1) reaction of the appropriate amino-quinoxaline with thiophosgene to form the corresponding isothiocyanate; and (2) reacting this isothiocyanate with excess ethylene diamine to form the corresponding beta-aminoethyl-thioureidoquinoxaline, which is then cyclized to the corresponding intermediate. Alternately, such intermediates can be prepared by (1) reacting the corresponding aminoquinoxaline with benzoyl isothiocyanate to form the corresponding N-benzoyl thioureido compound, followed by hydrolysis to the thioureido compound, or reaction of the aminoquinoxaline with ammonium thiocyanate to form the thioureido compound directly; (2) methylation to form the S-methyl deviation of the thioureido compound; and (3) reaction with ethylene diamine to form the intermediate.

The 2-imidazolin-2-ylamino quinoxaline intermediate is then reacted to saturate any unsaturation at the 1-, 2-, 3-, and 4- positions of the quinoxaline nucleus. For compounds in which $R_1$, $R_2$, $R_3$ and $R_4$ are all to be H, the intermediate may be hydrogenated. This hydrogenation preferably occurs with the intermediate dissolved in a liquid, e.g., a lower alcohol such as methanol, ethanol or the like. A catalyst effective to promote the hydrogenation is preferably present. Examples of such catalysts include the platinum group metals, in particular platinum, platinum group metal compounds, such as platinum oxide, and mixtures thereof. Hydrogen, e.g., free molecular hydrogen, is present in an amount at least sufficient to provide the desired saturation, preferably in an amount in excess of that required to provide the desired saturation, of the intermediate. The temperature and pressure at which the hydrogenation occurs are preferably selected to maintain the intermediate and final product substantially in the liquid phase. Temperatures in the range of about 10° C. to about 100° C. and pressures in the range of about 0.5 atmospheres to about 5 atmospheres often provide acceptable results. These conditions are maintained for a time sufficient to provide the desired hydrogenation reaction. This period of time is often in the range of about 1 minute to about 2 hours. The final 2-imidazolin-2-ylamino tetrahydroquinoxaline is separated from the hydrogenation reaction mixture and recovered, e.g., using conventional techniques.

For compounds in which $R_1$, $R_2$, $R_3$ and $R_4$ are all to be H and for compounds in which $R_1$ and $R_4$ are to be H and $R_2$ and/or $R_3$ are to be alkyl, the intermediate may be reacted with a suitable hydride reducing agent. This reaction preferably occurs with the intermediate and the hydride reducing agent dissolved in a liquid. Any suitable hydride reducing agent may be employed. Examples of useful hydride reducing agents include Na BH$_4$, NaCNBH$_4$, LiAlH$_4$ and the like. The amount of hydride reducing agent used should be sufficient to saturate all the unsaturation present at the 1-, 2-, 3- and 4- positions of the intermediate. Excess hydride reducing agent may be employed provided that no deterioration of the final tetrahydroquinoxaline product results. The liquid employed should be such as to act as an effective solvent for the intermediate and the hydride reducing agent, and may also function to facilitate, e.g., activate, the reaction between the intermediate and hydride reducing agent. Examples of useful liquids include acetic acid, trifluoroacetic acid, tetrahydrofuran, diethyl ether and the like. The liquid employed is preferably selected so as to avoid excess hydride reducing agent reactivity. For example, where LiAlH$_4$ is used as the hyride reducing agent, the liquid is preferably tetrahydrofuran, diethyl ether and the like. One or more co-solvents, e.g., lower alcohols, may also be used. The temperature and pressures at which the reaction occurs are preferably selected to maintain the intermediate and final product in the liquid phase. Temperatures in the range of about 0° C. to about 50° C. and pressure in the range of about 0.5 atmospheres to about 2 atmospheres often provide acceptable results. Reaction time is chosen to allow the desired reaction to occur, and is often in the range of about one minute to about one hour. The final 2-imidazolin-2-ylamino tetraquinoxaline is separated from the reactive mixture and recovered, e.g., using conventional techniques, such as evaporation, deactivation of the excess hydride reducing agent, extraction and chromatographic separation.

For compounds in which $R_1$ and/or $R_4$ are to be alkyl, the intermediate (having no substituents corresponding to $R_1$ and $R_4$) may be reacted with a suitable hydride reducing agent in the presence of a selected aldehyde or aldehydes. The aldehyde or aldehydes used are selected based on the specific $R_1$ and/or $R_4$ alkyl group or groups desired. For example, if $R_1$ and/or $R_4$ is to be methyl, formaldehyde is used, if $R_1$ and/or $R_4$ is to be ethyl, acetaldehyde is used, etc. The reaction conditions used are similar to those described in the immediately preceding paragraph except that the reaction time is often in the range of about 1 hour to about 24 hours. The amount of aldehyde used may vary depending on the final compound desired. A mixture of final compounds, i.e., a compound in which both $R_1$ and $R_4$ are alkyl mixed with compounds in which only one of $R_1$ or $R_4$ is alkyl, may be produced by the reaction. One or more individual tetrahydroquinoxalines of the present invention can be separated and recovered from this mixture, e.g., using conventional techniques.

The present 2-imidazolin-2-ylamino tetrahydroquinoxalines are useful to provide one or more desired therapeutic effects in a mammal. Among the desired therapeutic effects are an alteration, preferably a decrease, in the rate of fluid transport in the gastrointestinal tract of a mammal, a reduction in or maintenance of the intraocular pressure in at least one eye of a mammal; and an increase in the renal fluid flow in at least one kidney of a mammal. Thus, for example, the present compounds may be effective as an anti-diarrhea agent, a medication for use in the treatment or management of glaucoma, and/or a medication for use in the treatment or management of kidney disease. One important feature of many of the present compounds is that the desired therapeutic effect is achieved with reduced side effects, in particular with reduced effects on the blood pressure of the mammal to which the present compound is administered.

Any suitable method of administering the present compound or compounds to the mammal to be treated may be used. The particular method of administration chosen is preferably one which allows the present compound or compounds to have the desired therapeutic effect in an effective manner, e.g., low medication concentration and low incidence of side effects. In many applications, the present compound or compounds are administered to a mammal in a manner substantially similar to that used to administer alpha agonists, in particular alpha 2 agonists, to obtain the same or a similar therapeutic effect.

The present compound or compounds may be included in a medication composition together with one or more other components to provide a medication composition which can be effectively administered. Such other components, e.g., carriers, anti-oxidants, bulking agents and the like, may be chosen from those materials which are conventional and well known in the art, e.g., as being included in medication compositions with alpha 2 agonists.

The present compounds are often administered to the eye of a mammal to reduce or maintain intraocular pressure in the form of a mixture with an ophthalmically acceptable carrier. Any suitable, e.g., conventional, ophthalmically acceptable carrier may be employed. Such a carrier is ophthalmically acceptable if it has substantially no long term or permanent detrimental effect on the eye to which it is administered. Examples of ophthalmically acceptable carriers include water, in particular distilled water, saline and the like aqueous media. The present compounds are preferably administered to the eye as a liquid mixture with the carrier. The compounds are more preferably soluble in the carrier so that the compounds are administered to the eye in the form of a solution.

When an ophthalmically acceptable carrier is employed, it is preferred that the mixture contain one or more of the present compounds in an amount in the range of about 0.0001% to about 1%, more preferably about 0.05% to about 0.5%, W/V.

Any method of administering drugs directly to a mammalian eye may be employed to provide the present compound or compounds to the eye to be treated. By the term "administering directly" is meant to exclude those general systemic drug administration modes, e.g., injection directly into the patients blood vessels, oral administration and the like, which result in the compound or compounds being systemically available. The primary effect on the mammal resulting from the direct administering of the present compound or compounds to the mammal's eye is preferably a reduction in intraocular pressure. More preferably, the present compound or compounds are applied topically to the eye or are injected directly into the eye. Particularly useful results are obtained when the compound or compounds are applied topically to the eye.

Topical ophthalmic preparations, for example ocular drops, gels or creams, are preferred because of ease of application, ease of dose delivery, and fewer potential side effects. An exemplary topical ophthalmic formulation is shown below in Table I. The abbreviation q.s. means a quantity sufficient to effect the result or to make volume.

TABLE I

| Ingredient | Amount (% W/V) |
| --- | --- |
| (2-Imidazolin-2-ylamino) tetrahydroquinoxaline | about 0.0001 to about 1.0 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| antioxidant | as needed |
| Purified Water | as needed to make 100% |

Various preservatives may be used in the ophthalmic preparation described in Table I above. Preferred preservatives include, but are not limited to, benzalkonium chloride, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjustors may be added as needed or convenient. They include, but are not limited to, salts, particularly sodium chloride, potassium chloride, mannitol, and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetycysteine, butylated hydroxyanisole, and butylated hydroxytoluene.

Other excipient components which may be included in the exemplary ophthalmic preparation described in Table I are chelating agents which may be added as needed. The preferred chelating agent is edetate disodium, although other chelating agents may also be used in place of or in conjunction with it.

The following non-limiting examples illustrate certain aspects of the present invention.

EXAMPLE 1

Preparation of
5-Bromo-6-(2-imidazolin-2-ylamino)-1,2,3,4-tetrahydroquinoxaline 1,2,4-Triaminobenzene dihydrochloride To a suspension of 4-nitrophenylenediamine (Aldrich, 10 g, 65.3 mmol) in absolute ethanol (240 ml) was added 600 mg of 10% by weight palladium on charcoal catalyst. The container including the suspension was evacuated and filled with hydrogen three times and the suspension was hydrogenated at 18 psi until hydrogen uptake ceased. The reaction was slightly exothermic and one refill of hydrogen was required. The resulting light yellow solution, which darkens rapidly on contact with air, was filtered and concentrated to about 150 ml. Concentrated hydrochloric acid (12 ml) was added and the solid formed was filtered off. After drying in vacuo overnight, 12 g (a yield of 93%) of purple solid was obtained, m.p. 224°–5° C. Using various analytical procedures, this solid was determined to be 1,2,4-triaminobenzene dihydrochloride.

6-Aminoquinoxaline

Glyoxal sodium bisulfite adduct (Aldrich, 14.3 g, 50 mmol) was added in small portions to a solution of 1,2,4-triaminobenzene dihydrochloride (9.8 g, 50 mmol) in 200 ml of 10% by weight sodium carbonate in water. The reaction mixture was heated to 100° C. for two hours and then cooled to 0° C. The crystals formed were filtered off and dried in vacuo to give a crude yield of 7.06 g (a yield of 97%) of brown crystals. Recrystallization from benzene gave 6.32 g (a yield of 87%) yellow crystals, m.p. 157°–8° C. Using various analytical procedures, these yellow crystals were determined to be 6-aminoquinoxaline.

6-Amino-5-bromoquinoxaline hydrobromide

6-Aminoquinoxaline (2.08 g, 14.4 mmol) was dissolved in 11.5 ml glacial acetic acid. The solution was cooled in water while a solution of bromine (0.74 ml, 2.3 g, 14.4 mmol) in 1.5 ml glacial acetic acid was added slowly over 15 min. After stirring for an additional 30 min, the orange red solid formed was filtered off and washed thoroughly with dry ether. The solid was dried in vacuo overnight to yield 4.44 g crude product (a yield of 100%). The compound, 6-amino-5-bromoquinoxaline hydrobromide, had no definite melting point. A phase change (from fine powder to red crystals) was noticed at about 220° C. Decomposition was observed at about 245° C. It was used directly for the next step.

6-Amino-5-Bromoquinoxaline

The crude 6-amino-5-bromoquinoxaline from above was dissolved in water and saturated sodium bisulfite solution was added until the resulting solution tested negative with starch-iodide paper. The solution was then basified with 2N sodium hydroxide and extracted thoroughly with ethyl acetate. The organic extract was dried over magnesium sulfate and concentrated under reduced pressure to give the free base. The crude product was recrystallized from boiling benzene to give yellow crystals, m.p. 155°-6° C. Using various analytical procedures, the yellow crystals were determined to be 6-amino-5-bromoquinoxaline. The yield was 82%.

5-Bromo-6-isothiocyanatoquinoxaline

The crude hydrobromide product previously noted (4.27 g, 14.0 mmol) was dissolved in 60 ml of water and thiophosgene (Aldrich, 1.28 ml, 16.8 mmol) was added in small portions with vigorous stirring. After 2 hours, the red color of the solution was discharged. The solid formed was filtered off and washed thoroughly with water. After drying in vacuo at 25° C., 3.38 g (a yield of 90%) of brick red crystals was obtained, m.p. 157°-8° C. A portion of this material was further purified by column chromatography to give white crystals, m.p. 157°-8° C. Using various analytical procedures, these crystals were determined to be 5-bromo-6-isothiocyanatoquinoxaline.

5-Bromo-6(-N-(2-aminoethyl)thioureido)quinoxaline

A solution of the isothiocyanate (3.25 g, 12.2 mmol) in 145 ml benzene was added to a solution of ethylenediamine (Aldrich, 5.43 g, 90.0 mmol) in 18 ml benzene at 25° C. over 2 hours. After stirring for a further 30 min., the supernatant was poured off. The oil which remained was washed by swirling with dry ether three times and used directly for the next step.

A portion of this product was further purified by column chromatography (SiO$_2$, CHCl$_3$) for characterization. A white solid was recovered which decomposed at 175° C. with gas evolution (puffing). This white solid was determined to be 5-bromo-6(-N-2-(aminoethyl)thioureido)quinoxaline.

5-Bromo-6-(2-imidazolin-2-ylamino)quinoxaline

The crude product from above was dissolved in 100 ml dry methanol and the brown solution was refluxed for 19 hours until hydrogen sulfide gas was no longer evolved. The mixture was cooled to room temperature and concentrated to about 50 ml. The yellow solid was filtered off and dried in vacuo; weight 2.52 g (a yield of 70%), mp 242°-4° C.

As the crude product was insoluble in most common organic solvents, initial purification was achieved by an acid-base extraction procedure. 23 g of the crude product was dissolved in 100 ml 0.5N hydrochloric acid. The turbid yellow solution was filtered to give a clear orange yellow solution which was extracted twice with ethyl acetate (2 × 10 ml). The aqueous phase was cooled to 0° C. and basified with 6N sodium hydroxide, keeping the temperature of the solution below 15° C. at all times. The yellow solid which precipitated was filtered off and washed thoroughly with water until the washings were neutral to pH paper. The solid was dried overnight in vacuo to give 1.97 g yellow solid, m.p. 249°-50° C. The recovery was about 88%.

Further purification was achieved by recrystallization as described below. The partially purified product from above was dissolved in N,N-dimethylformamide (about 17 ml/g) at 100° C. with vigorous stirring. The solution was filtered hot and set aside to cool overnight. The bright yellow crystals were collected by filtration, m.p. 252°-3° C. Recovery was from 65-77%. Using various analytical procedures, the bright yellow solid was determined to be 5-bromo-6-(2-imidazolin-2-ylamino) quinoxaline.

5-Bromo-6-(2-imidazolin-2-ylamino)-1,2,3,4-tetrahydroquinoxaline

A thick-walled Parr hydrogenation flask was charged with 5-Bromo-6-(2-imidazolin-2-ylamino)quinoxaline (950 mg, 3.23 mmol), platinum oxide (95 mg) and 20 ml of methanol. The contents of the flask were contacted with hydrogen at 15 psi for 15 minutes. The resulting solution was filtered through acid washed silicon dioxide, followed by evaporation of solvent. The resulting tan solid was chromatographed (SiO$_2$; 80/20 CHCl$_3$/CH$_3$OH saturated with NH$_3$ (g)) to yield 820 mg (a yield of 86%) of an off white soid, mp 218°-220° C. Using various analytical procedures, this off white solid was determined to be 5-bromo-6-(2-imidazolin-2-ylamino)-1,2,3,4-tetrahydroquinoxaline.

EXAMPLE 2

Preparation of (±)2-Methyl-5-bromo-6-(2-imidazolin-2-ylamino)-1,2,3,4-tetrahydroquinoxaline

2-Methyl-6-nitroquinoxaline

A solution of pyruvic aldehyde (Aldrich, 40% solution in H$_2$O, 11.8 g, 65.3 mmol) was added dropwise to a solution of 4-nitro-1,2-phenylenediamine (Aldrich, 10 g, 65.3 mmol) in 150 ml of H$_2$O. The reaction mixture was heated to 80° C. for four hours. The reaction was cooled to room temperature, diluted with H$_2$O and extracted with CHCl$_3$. The organic extracts were dried over MgSO$_4$ and evaporated to yield 10.7 g (a yield of 87%) of as a brick red solid. Using various analytical procedures, this solid was determined to be 2-methyl-6 nitroquinoxaline.

2-Methyl-6-Aminoquinoxaline

A thick-walled Parr hydrogenation flask was charged with 2-methyl-6-nitroquinoxaline (10.0 g, 52.9) and CH$_3$OH (200 ml). The flask was flushed with a stream of N$_2$ and 10% by weight palladium on charcoal (500 mg) was added. The flask was pressurized with H$_2$ to 50 psi and maintained at this pressure for three hours. The reaction mixture was filtered through acid washed silicon dioxide and concentrated in vacuo to yield a tan solid. The crude material was chromatographed (SiO$_2$; 95/5 CHCl$_3$/CH$_3$OH saturated with NH$_3$ (g)) and recrystallized from benzene to yield 7.4 g (a yield of 88%) of a tan solid. Using various analytical procedures, this tan solid was determined to be 2-methyl-6-aminoquinoxaline.

2-Methyl-5-bromo-6-(2-imidazolin-2-ylamino)quinoxaline

By a series of reaction steps analogous to the reaction steps described above in Example 1, the title compound (mp. 260° C.) was prepared starting with 2-methyl-6-aminoquinoxaline in place of 6-aminoquinoxaline.

(+)2-methyl-5-Bromo-6-(2-imidazolin-2-ylamino)-1,2,3,4-tetrahydroquinoxaline

A solution of 2-methyl-5-bromo-6-(2-imidazolin-2-ylamino) quinoxaline (40.5 mg, 0.132 mmol) in acetic acid was cooled to 10° C. and carefully treated with NaBH$_4$ (5.0 mg, 0.132 mmol). The reaction mixture was stirred for 15 minutes before the solvent was removed in vacuo. The residue was dissolved in H$_2$O, treated with solid NaOH to pH 13 and extracted with CHCl$_3$. The combined organic extracts were dried over MgSO$_4$ and concentrated in vacuo to yield a yellow oil. The crude material was chromatographed (SiO$_2$, 80/20 CHCl$_3$/CH$_3$OH saturated with NH$_3$ (g)) to yield 21.8 mg (a yield of 53%) of a tan solid, mp 203°–205° C. Using various analytical procedures, this tan solid was determined to be (±) 2-methyl-5-bromo-(2-imidazolin-2-ylamino)-1,2,3,4-tetrahydroquinoxaline.

EXAMPLE 3

Preparation of (±) 3-Methyl-5-bromo-6-(2-imidazolin-2 ylamino)-1,2,3,4-tetrahydroquinoxaline 3-Methyl-6-aminoquinoxaline Pyruvic aldehyde (Aldrich, 892 mg, 4.95 mmol, 40% solution H$_2$O) was added dropwise to a stirred solution of 1, 2, 4-triaminobenzene hydrochloride (1.0 g, 4.95 mmol) dissolved in 10% aqueous Na$_2$CO$_3$ (15 ml). The mixture was heated at 100° C. for two hours before cooling to room temperature. The mixture was extracted with CHCl$_3$. The combined organic extracts were dried over MgSO$_4$ and concentrated in vacuo to yield a brown solid. The crude product was chromatographed (SiO$_2$, 95/5 CHCl$_3$CH$_3$OH saturated with NH$_3$ (g)) to yield 616 mg (a yield of 75%) of a yellow crystalline solid. An analytical sample was prepared by recrystallization from benzene, mp 170°–173° C. Using various analytical procedures, the solid was determined to be 3-methyl-6-aminoquinoxaline.

(±) 3-Methyl-5-bromo-6-(2-imidazolin-2-ylamino)-1,2,3,4-tetrahydroquinoxaline

By a series of reaction steps analogous to the reaction steps described above in Example 2, the title compound (mp 250°–251° C.) was prepared starting with 3-methyl-6-aminoquinoxaline in place of 2-methyl-6-aminoquinoxaline.

EXAMPLE 4

Preparation of 5-Bromo-6-(2-imidazoline-2-ylamino)-1,4-dimethyl-1,2,3,4-tetrahydroquinoxaline, 5-Bromo-6-(2-imidazolin-2-ylamino)-1-methyl-1,2,3,4-tetrahydroquinoxaline and 5-Bromo-6-(2-imidazolin-2-ylamino)-4-methyl-1,2,3,4-tetrahydroquinxoaline.

5-Bromo-6-(2-imidazolin-2-ylamino) quinoxaline (291 mg, 1 mmol) is suspended in CH$_3$OH (2 ml) and treated with glacial acetic acid (1 ml). The reaction mixture is treated with NaCNBH$_3$ (252 mg, 4 mmol) and paraformaldehyde (450 mg, 5 mmol) and stirred at room temperature for 4–8 hours. The reaction mixture is quenched with H$_2$O (5 ml), basified with solid NaOH (3 g) to pH>12 and extracted with CHCl$_3$. The CHCl$_3$ extracts are dried over MgSO$_4$, concentrated invacuo and chromatographed (SiO$_2$, 80/20 CHCl$_3$/CH$_3$OH saturated with NH$_3$ (g)) to yield the individual title compounds. Each of these title compounds is tested and is found to have one or more useful therapeutic effects which known alpha 2 agonists exhibit.

EXAMPLE 5

Preparation of 5-Bromo-6-(2-imidazolin-2-ylamino)-1,4-diethyl-1,2,3,4-tetrahydroquinoxaline, 5-Bromo-6-(2-imidazolin-2-ylamino)-1-ethyl-1,2,3,4-tetrahydroquinoxaline and 5-Bromo-6-(2-imidazolin-2-ylamino)-4-ethyl-1,2,3,4-tetrahydroquinoxaline The individual title compounds are prepared using the method illustrated in Example 5 except that acetaldehyde (220 mg, 5 mmol) is substituted for paraformaldehyde and the reaction time is 6–12 hours instead of 4–8 hours. Each of these title compounds is tested and is found to have one or more useful therapeutic effects which known alpha 2 agonists exhibit.

EXAMPLES 6 TO 8

The three (3) tetrahydroquinoxaline derivatives produced in accordance with Examples 1 to 3 were tested to determine what effect, if any, these materials have on intraocular pressure.

Each of these materials was dissolved in distilled water at a concentration of 0.1% (W/V). Each of these solutions was administered topically and unilaterally to one eye of a drug-naive, unanesthetized New Zealand white rabbit in a single 50 micro liter drop. The contralateral eye received an equal volume of saline prior to determining the intraocular pressure after the mixture was administered. Also, approximately 10 micro liters of 0.5% (W/V) proparacaine (topical anesthetic) was applied to the corneas of each of the rabbits before determining intraocular pressure. As a control test, six (6) other drug-naive, unanesthetized New Zealand white rabbits were treated and tested as described above except that no tetrahydroquinoxaline derivative was included in the solutions administered to the eyes.

The intraocular pressure was determined in both eyes of each rabbit before and after the solutions were administered. Such intraocular pressure determinations were made in the conventional manner using conventional equipment.

Results of these IOP determinations were as follows:

| Example | Active Material | Difference In Intraocular Pressure, percent | | |
|---|---|---|---|---|
| | | Initial Effect On Treated Eye | Maximum Effect on Treated Eye | Maximum Effect On Untreated Eye |
| 6 | [structure: 5-bromo-6-(2-imidazolin-2-ylamino)-1,2,3,4 tetrahydroquinoxaline] | +10.7 ± 3.6 | −16.0 ± 3.3 | N.S. |
| 7 | (±) [structure: 2-methyl-5-bromo-6-(2-imidazolin-2-ylamino)-1,2,3,4 tetrahydroquinoxaline] | N.S. | −15.1 ± 3.3 | −8.6 ± 2.4 |
| 8 | (±) [structure: 3-methyl-5-bromo-6-(2-imidazolin-2-ylamino)-1,2,3,4 tetrahydroquinoxaline] | N.S. | −12.5 ± 2.2 | N.S. |
| Control | | N.S. | N.S. | N.S. |

N.S. means that the effect was not statistically significant.

N.S. means that the effect was not statistically significant.

These results indicate that all of 5-bromo-6-(2-imidazolin-2-ylamino)-1,2,3,4 tetrahydroquinxaline (Example 6), (±) 2-methyl-5-bromo-6-(2-imidazolin-2-ylamino)-1,2,3,4 tetrahydroquinoxaline (Example 7), and (±) 3-methyl-5-bromo-6-(2-imidazolin-2-ylamino)-1,2,3,4 tetrahydroquinoxaline (Example 8) are effective to reduce intraocular pressure in the treated rabbit eye, i.e., the eye to which the active material was directly administered. The tetrahydroquinoxaline derivative in Example 6 had an initial effect in the treated eye of raising the intraocular pressure. The tetrahydroquinoxaline derivative in Example 7 also resulted in reducing the intraocular pressure in the untreated rabbit eye.

EXAMPLES 9 TO 11

The tetrahydroquinoxalines produced in Examples 1 to 3 were tested for activity using the following in vitro methods.

Rabbit Vas Deferens: Alpha 2 Adrenergic Receptors

New Zealand white rabbits (2–3 kg) were killed by $CO_2$ inhalation and the vasa deferentia removed. The prostatic ends of the vasa deferentia (2–3 cm lengths) were mounted between platinum ring electrodes in 9 ml organ baths and bathed in Krebs bicarbonate solution of the following composition (millimolar): NaCl 118.0; KCl 4.7; $CaCl_2$ 2.5; $MgSO_4$ 1.2; $KH_2PO_4$ 1.2; glucose 11.0; $NaHCO_3$ 25.0; which solution was maintained at 35° C. and bubbled with 95% $O_2$ and 5% $CO_2$. The initial tension of the vas deferens was 0.5 g. The tissues were left to equilibrate for 30 minutes before stimulation was started. Vasa were then field stimulated (0.1 Hz, 2 ms pulse width at 90 mA) using a square wave stimulator (WPI A310 Accupulser with A385 stimulus). The contractions of the tissue were recorded isometrically using Grass FTO3 force-displacement transducers and displayed on a Grass Model 7D polygraph. Cumulative concentration-response curves were obtained for the tetrahydroquinoxaline being tested with a 4 minute contact time at each concentration. The reduction in response height was measured and expressed as a percentage of the height of the response before the addition of tetrahydroquinxaoline. Concentration response curves for each of tetrahydroquinoxalines were plotted. The effective concentration required for a 50% reduction in response height, expressed as $EC_{50}$, were obtained from these curves and are set forth below.

Rabbit Aorta: Alpha 1 Adrenergic Receptors

Rabbit Saphenous Vein: Alpha 3 Adrenergic Receptors

Thoracic aorta and saphenous vein specimens were obtained from albino rabbits that were killed by $CO_2$ inhalation. The aorta and saphenous vein were each cut into 3 mm rings. Tissues were placed in Krebs-Hensleit solution of the following composition (millimolar): NaCl 119; KCl 4.7; $MgSO_4$ 1.5, $KH_2PO_4$ 1.2; $CaCl_2$ 2.5; $NaHCO_3$ 25 and glucose 11.0. The solution also contained cocaine (0.1 millimolar) to block neuronal uptake and EDTA (30 micromolar) and ascorbic acid (5 micromolar) to prevent oxidation of the tetrahydroquinoxaline being tested. Tissues were hung in 10 ml organ baths and tension was measured via Grass FT03 force-displacement transducers. Resting tension was 1 g and 2 g for the saphenous vein and aorta, respectively. The solution was gassed with 95% $O_2$ and 5% $CO_2$ and maintained at 37° C. Tissues were allowed to equilibrate for 2 hours before stimulation and the cumulative addition of the tetrahydroquinoxaline being treated was started. Tissue stimulation was performed as with the rabbit vas deferens, described above. The contractions of the tissue were recorded isometrically as for the rabbit vas deferens assay. Cumulative concentration response curves were obtained and the EC50 valve developed for each tetrahydroquinoxaline tested in a manner similar to that for the rabbit vas deferens assay.

Results of these in vitro tests were as follows:

and vena cava via the femoral vessels. In addition, a Silastic-covered stainless steel cannula were sewn in the urinary bladder. After the surgery, the rats were housed individually and were allowed free access to food and water until the day of the experiment.

For about 7 to 10 days before surgery and during recovery, the rats were accustomed to a restraining cage by placement in the cage for 2 to 3 hours every 2nd and 3rd day. The cage was designed for renal clearance studies (a model G Restrainer sold by Braintree Scientific, Inc., Braintree, Mass.). The animals' adjustment to the cage was judged by the stability of blood pressure and heart rate.

For an experiment, a rat was placed in the restraining cage, and the arterial line was connected to a Statham pressure transducer and a Beckman Dynograph R61 to

| Example | Active Material | $EC_{50}$, nanomolar Rabbit Aorta | Rabbit Vas Deferens | Rabbit Saphenous Vein |
|---|---|---|---|---|
| 9 | [structure] | 1130 ± 207 (n = 8) | 1.75 (n = 1) | 92 ± 19 (n = 6) |
| 10 | (±) [structure with CH3] | 6750 ± 116 (n = 3) | 35.3 ± 3.9 (n = 5) | 581 ± 29 (n = 2) |
| 11 | (±) [structure with CH3] | 1060 ± 271 (n = 3) | 21.3 ± 3.0 (n = 2) | — | n is equal to the number of times the particular test was run.

These results indicate that the present tetrahydroquinoxalines have some activity with respect to all of the alpha 1, alpha 2 and alpha 3 adrenergic receptors. However, these materials have a particularly high activity with respect to the alpha 2 adrenergic receptors. Thus, the present tetrahydroquinoxalines are properly classified as alpha 2 agonists.

EXAMPLE 12

The tetrahydroquinoxaline produced in Example 1 was tested for renal and blood pressure effects using the following method.

Young male (20–24 weeks old) Sprague-Dawley rats were used. Under ketamine (60 mg/kg b.wt. i.m.) and pentobarbital (i.p. to effect) anesthesia, medical grade plastic tubes were implanted into the abdominal aorta monitor the mean arterial blood pressure, hereinafter referred to as MAP. The venous line was connected to an infusion pump system for infusion of replacement fluid. The tetrahydroquinoxaline was administered intraduodenally by cannula. The bladder cannula was extended with a silastic tube to facilitate collection of urine in preweighed tubes. The volume of urine was measured gravimetrically. Body weight was recorded before and after the experiment.

Throughout the experiments, 0.9% NaCl containing 10% polyfructosan (Inutest) and 1% sodium PAH was infused at a rate of 20 microliters/min. An equilibration period of 60 minutes was followed by two consecutive 30 minute control clearance periods. Then, the tetrahydroquinoxaline was administered for 90 minutes. Urine collection was resumed 10 minutes after the start of tetrahydroquinoxaline administration. By this time the washout of the bladder cannula dead space (approximately 200 microliters) was completed. Three additional clearance measurements were made. Blood samples (150 microliters) were collected at the midpoint of urine collections. Plasma was separated and saved for analyses, and the cells were resuspended in saline and returned to the animals. Water and sodium loss was carefully replaced i.v. by a variable speed infusion pump.

Results of these tests were as follows:

| Dose of Tetrahydro-quinoxaline of Example 1, mg/kg of body weight | Increase in Urine Flow, microliters/min./100 g of body weight | Increase in MAP, mm Hg |
|---|---|---|
| 0.01 | 0 | 0 |
| 0.03 | 4 | 0 |
| 0.1 | 16 | 0 |
| 0.3 | 24 | 2.5 |
| 1 | 32 | 8 |

The test was run 3 times. The results at 0.1 mg/kg of body weight and higher dosages represent statistically significant differences (i.e., in a conventional statistical analysis of the date, P is less than 0.05).

These results indicate that the present substituted quinoxalines produce relatively large renal effects. Further, these results show that such renal effects are produced without a correspondingly large effect on the blood pressure.

EXAMPLE 13

The tetrahydroquinoxaline produced in Example 1 was tested for anti-diarrheal effects and blood pressure effects using the following method.

Cecectomies were performed in unfasted rats as follows. Under anesthesia with methohexital (60 mg/kg. i.p.), a laparotyphlectomy was initiated with a 2 cm midventral incision. The cecum was lifted from the abdominal cavity and exteriorized onto a gauze drape. The cecal apex was freed by severing the avascular area of the mesocecum. Next, a ligature of #1 silk suture was positioned so as to occulude the cecum and its vasculature without compromising ileo-colonic patency. After the ligature was secured and ileo-colonic patency confirmed, the cecum was resected, and the remaining exposed cecal mucosa was washed with saline and cauterized. The intestinal segment was then returned to the abdominal cavity, and the abdominal muscle facia closed with interrupted 4/0 chromic-gut sutures. The dermal incision was closed with 9 mm stainless steel wound clips that were removed approximately 1 week post surgery. An arterial line was also implanted into the abdominal aorta and vena cava via the femoral vessels, in a manner similar to that described in Example 10. Immediately following the surgical procedure, animals were returned to their cages and allowed free access to food and water. Animals were permitted at least 48 hour recovery period before being used in experiments.

The cecectomized rats were put into individual wire-bottomed cages placed over sheets of clean paper, and deprived of food and water for the duration of the assay. The MAP was monitored, as described in Example 10, throughout the assay. Rats were given a 2 hour acclimatization period prior to the start of the assay in order to eliminate sporadic episodes of anxiety-induced defecation. During this period they were observed also for consistent occurrences of pelleted feces; an animal producing other than a pelleted stool was disqualified from the study.

Diarrhea was induced with oral administration of 16,16-dimethyl prostaglandin $E_2$ (dmPGE$_2$) in 3.5% EtOH. The tetrahydro-quinoxaline was administered by gavage after the onset of diarrheal episodes. The cage papers were removed and examined at 30 minute intervals for dmPGE$_2$-induced diarrhea. Fecal output was recorded at each interval and fecal consistency is assigned a numerical score in each experimental group as follows: 1=normal pelleted stool; 2=soft-formed stools; 3=water stool and/or diarrhea. The fecal output index (FOI) is defined as the summation of the number of defecation episodes and their ranked consistency score within an observation period.

Results of these tests were as follows:

| Dose of Tetrahydro-quinoxaline of Example 1, mg/kg of Body Weight, p.o. | Percent Reduction in FOI versus dmPGE$_2$ Control | Increase in MAP, mm Hg |
|---|---|---|
| 0.01 | 17 | 0 |
| 0.03 | 60 | 0 |
| 0.10 | 57 | 0 |
| 0.30 | 76 | 0 |
| 1.00 | 98 | 0 |
| 3.00 | 98 | 10 |
| 10.00 | 100 | 25 |

These results indicate that the tetrahydroquinoxaline produced in Example 1 provided substantial anti-diarrheal effects. Further, these results show that such anti-diarrheal effects are produced with no or a relatively minimal effect in blood pressure.

While this invention has been described with respect to various specific examples and embodiments, it is to be understood that the invention is not limited thereto and that it can be variously practices within the scope of the following claims.

What is claimed is:

1. A compound selected from the group consisting of those having the formula

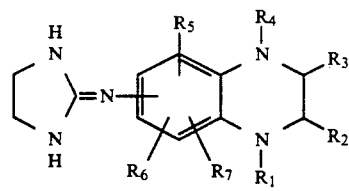

and pharmaceutically acceptable acid addition salts thereof, wherein $R_1$ and $R_4$ are independently selected from the group consisting of H and alkyl radicals having 1 to 4 carbon atoms, $R_2$ and $R_3$ are independently selected from the group consisting of H, oxo, and alkyl radicals having 1 to 4 carbon atoms, the 2-imidazolin-2-ylamino group may be in any of the 5-, 6-, 7- or 8- positions of the quinoxaline nucleus, and $R_5$, $R_6$ and $R_7$ each is located in one of the remaining 5-, 6-, 7- or 8- positions of the quinoxaline nucleus and is independently selected from the group consisting of Cl, Br, H and alkyl radicals having 1 to 3 carbon atoms.

2. The compound of claim 1 wherein the 2-imidazolin-2-ylamino group is in the 6- position of the quinoxaline nucleus, $R_5$ is in the 5- position of the quinoxaline nucleus and is selected from the group consisting of Cl, Br and alkyl radicals having 1 to 3 atoms, and $R_6$ and $R_7$ are both H.

3. The compound of claim 2 wherein each of $R_1$ and $R_4$ is H.

4. The compound of claim 2 wherein $R_2$ and $R_3$ are independently selected from the group consisting of H and methyl radical.

5. The compound of claim 3 wherein $R_2$ and $R_3$ are independently selected from the group consisting of H and methyl radical.

6. The compound of claim 4 wherein $R_2$ and $R_3$ are different.

7. The compound of claim 5 wherein $R_2$ and $R_3$ are different.

8. The compound of claim 2 wherein $R_5$ is Br.

9. The compound of claim 3 wherein $R_5$ is Br.

10. The compound of claim 4 wherein $R_5$ is Br.

11. The compound of claim 6 wherein $R_5$ is Br.

12. The compound of claim 1 wherein the formula is:

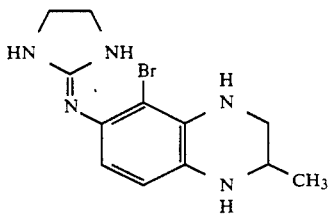

13. The compound of claim 1 wherein the formula is:

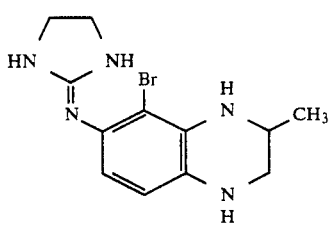

14. A compound selected from the group consisting of

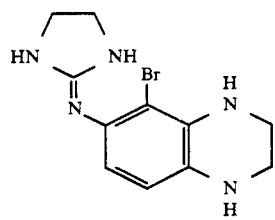

and pharmaceutically acceptable acid addition salts thereof.

15. A medication composition comprising:
an amount of a compound effective to provide a desired therapeutic effect in a mammal to which said amount of said compound is administered, said desired therapeutic effect being selected from the group consisting of (1) an alteration in the rate of fluid transport in the gastrointestinal tract of said mammal; (2) a reduction in the intraocular pressure in at least one eye of said mammal; and (3) an increase in the renal fluid flow in at least one kidney of said mammal, said compound being selected from the group consisting of those having the formula

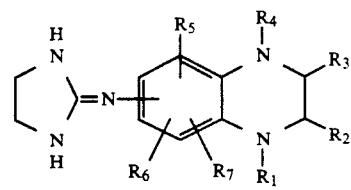

pharmaceutically acceptable acid addition salts thereof and mixtures thereof, wherein $R_1$ and $R_4$ are independently selected from the group consisting of H and alkyl radicals having 1 to 4 carbon atoms, $R_2$ and $R_3$ are independently selected from the group consisting of H, oxo, and alkyl radicals having 1 to 4 carbon atoms, the 2-imidazolin-2-ylamino group may be in any of the 5-, 6-, 7- or 8- positions of the quinoxaline nucleus, and $R_5$, $R_6$ and $R_7$ each is located in one of the remaining 5-, 6-, 7 - or 8- positions of the quinoxaline nucleus and is selected from the group consisting of Cl, Br, H and alkyl radicals having 1 to 3 carbon atoms; and a carrier component combined with said compound in an amount effective to facilitate the administration of said amount of said compound to said mammal.

16. The medication composition of claim 15 wherein the 2-imidazoline-2-ylamino group is in the 6- position of the quinoxaline nucleus, $R_5$ is in the 5- position of the quinoxaline nucleus and is selected from the group consisting of Cl, Br and alkyl radicals having 1 to 3 atoms, and $R_6$ and $R_7$ are both H.

17. The medication composition of claim 16 wherein each of $R_1$ and $R_4$ is H.

18. The medication composition of claim 16 wherein $R_2$ and $R_3$ are independently selected from the group consisting of H and methyl radical.

19. The medication composition of claim 18 wherein $R_2$ and $R_3$ are different.

20. The medication composition of claim 16 wherein $R_5$ is Br.

21. The medication composition of claim 15 wherein said formula is

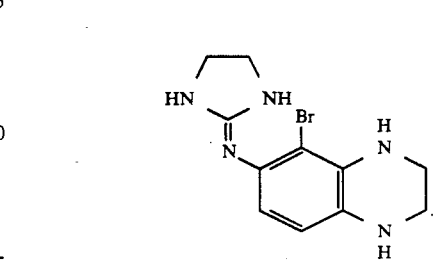

22. The medication composition of claim 15 wherein said formula is

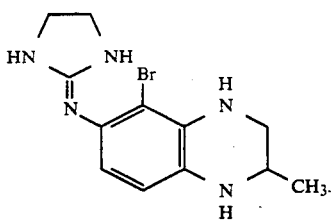

23. The medication composition of claim 15 wherein said formula is

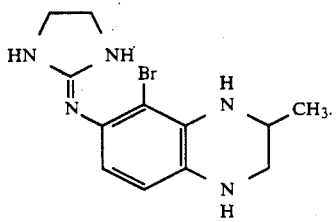

24. A method for reducing or maintaining the intraocular pressure in a mammalian eye comprising administering to a mammalian eye an effective amount to reduce or maintain the intraocular pressure in the mammalian eye of a compound selected from the group consisting of those having the formula

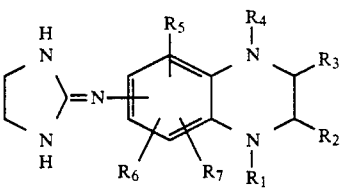

pharmaceutically acceptable acid addition salts thereof and mixtures thereof, wherein $R_1$ and $R_4$ are independently selected from the group consisting of H and alkyl radicals having 1 to 4 carbon atoms; $R_2$ and $R_3$ are independently selected from the group consisting of H, oxo, and alkyl radicals having 1 to 4 carbon atoms, the 2-imidazolin-2-ylamino group may be in any of the 5-, 6-, 7- or 8- positions of the quinoxaline nucleus; and $R_5$, $R_6$ and $R_7$ each is located in one of the remaining 5-, 6-, 7- or 8- positions of the quinoxaline nucleus and is selected from the group consisting of Cl, Br, H and alkyl radicals having 1 to 3 carbon atoms.

25. The method of claim 24 wherein said compound is administered directly to the mammalian eye.

26. The method of claim 24 wherein said compound is administered directly to the mammalian eye in an amount effective to reduce the intraocular pressure in the mammalian eye.

27. The method of claim 24 wherein the 2-imidazolin-2-ylamino group is in the 6- position of the quinoxaline nucleus, $R_5$ is in the 5- position of the quinoxaline nucleus and is selected from the group consisting of Cl, Br and alkyl radicals having 1 to 3 atoms, and $R_6$ and $R_7$ are both H.

28. The method of claim 27 wherein $R_2$ and $R_3$ are independently selected from the group consisting of H and methyl radical.

29. The method of claim 27 wherein $R_5$ is Br.

30. The method of claim 25 wherein said formula is:

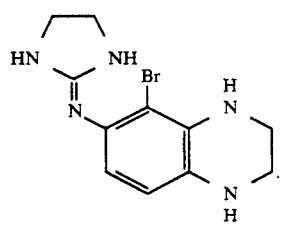

31. The method of claim 24 wherein said formula is:

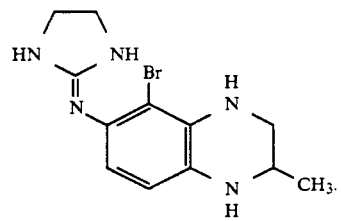

32. The method of claim 24 wherein said formula is:

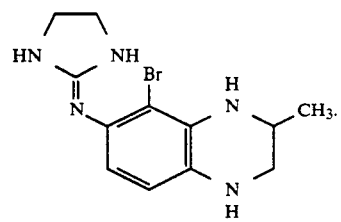

* * * * *

UNITED STATES PATENT AND TRADEMARK OFFICE
CERTIFICATE OF CORRECTION

PATENT NO. : 5,077,292
DATED : December 31, 1991
INVENTOR(S) : CHARLES GLUCHOWSKI It is certified that error appears in the above-identified patent and that said Letters Patent is hereby corrected as shown below:

Title page, item [57]
In the Abstract at the 7th line from the end of the Abstract, change "qunioxaline" to -- quinoxaline -- .

Column 8, line 33, change "soid" to -- solid -- .

Column 9, line 48, change "CHCl$_3$CH$_3$OH" to -- CHCl$_3$/CH$_3$OH -- .

Column 15, line 43, change "occulude" to -- occlude -- .

Column 19, line 40, please insert a -- , -- before "pharmaceutically".

Column 20, line 15, change "25" to -- 24 -- .

Signed and Sealed this

Ninth Day of November, 1993

Attest:

BRUCE LEHMAN

Attesting Officer    Commissioner of Patents and Trademarks